United States Patent [19]
Nakano et al.

[11] Patent Number: 5,833,343
[45] Date of Patent: Nov. 10, 1998

[54] LIGHT-SOURCE SWITCHING AND DRIVING UNIT

[75] Inventors: Etuo Nakano; Suwao Satoh, both of Okaya, Japan

[73] Assignee: Fuji Photo Optical Co., Ltd., Omiya, Japan

[21] Appl. No.: 665,558

[22] Filed: Jun. 18, 1996

[30] Foreign Application Priority Data

Jun. 27, 1995 [JP] Japan ................................ 7-183558

[51] Int. Cl.⁶ .................................................. F21V 19/04
[52] U.S. Cl. .......................... 362/20; 362/35; 362/286; 362/287; 362/386
[58] Field of Search ........................... 362/20, 418, 287, 362/35, 286, 386; 310/68 B, 68 C, 68 D

[56] References Cited

U.S. PATENT DOCUMENTS

| | | | |
|---|---|---|---|
| 3,577,173 | 5/1971 | Blomgren | 315/88 |
| 3,964,040 | 6/1976 | Behl | 340/251 |
| 4,034,259 | 7/1977 | Schoch | 315/93 |
| 4,112,344 | 9/1978 | Klein | 318/685 |
| 4,137,913 | 2/1979 | Georgi | 128/214 |
| 4,311,586 | 1/1982 | Baldwin et al. | 210/101 |
| 4,402,038 | 8/1983 | Hartung et al. | 362/20 |
| 4,415,951 | 11/1983 | Recane et al. | 362/20 |
| 4,460,353 | 7/1984 | Deckert et al. | 604/31 |
| 5,534,854 | 7/1996 | Bradbury et al. | 340/648 |

*Primary Examiner*—Ira S. Lazarus
*Assistant Examiner*—David Lee
*Attorney, Agent, or Firm*—Ronald R. Snider

[57] ABSTRACT

The present invention is a light-source switching and driving unit where an accurate stop operation and a strong holding force are obtained and which is capable of reducing a noise and preventing an impact to light-source lamps. In this unit, a plurality of light-source lamps for being switched and used are disposed. When a burnout sensor detects the burnout of a lamp being currently used, a spare light-source lamp is moved to a predetermined position by a stepping motor. In switching one lamp to another lamp, a pulse generating circuit generates a drive pulse which gradually increases when the stepping motor is started and a drive pulse which gradually decreases when the stepping motor is stopped. The stepping motor is driven by these drive pulses. With this, in switching one lamp to another lamp, a slow operation can be realized when the motor is started and when the motor is stopped.

10 Claims, 5 Drawing Sheets

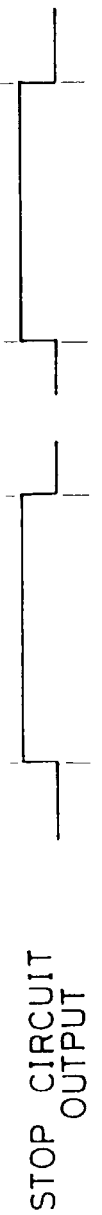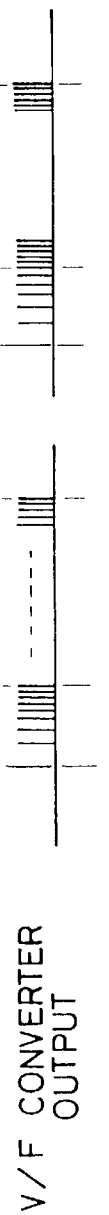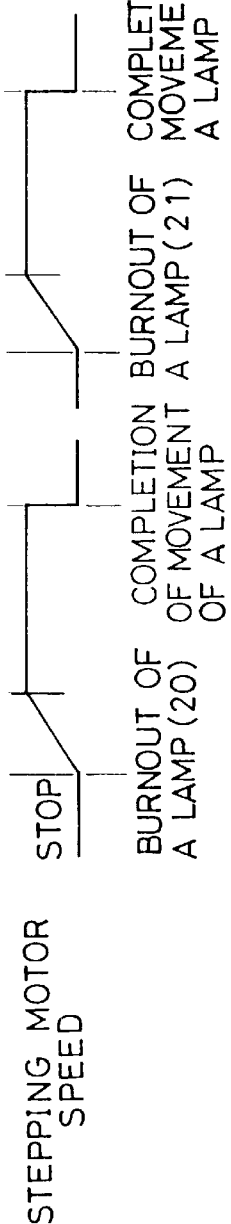
FIG.4A PHOTOINTERRUPTER OUTPUT (20)
FIG.4B PHOTOINTERRUPTER OUTPUT (21)
FIG.4C BURNOUT SENSOR OUTPUT
FIG.4D INVERTING CIRCUIT OUTPUT
FIG.4E MONOSTABLE MULTI-VIBRATOR OUTPUT
FIG.4F STOP CIRCUIT OUTPUT
FIG.4G INTEGRATION CIRCUIT OUTPUT
FIG.4H V/F CONVERTER OUTPUT
FIG.4I STEPPING MOTOR SPEED

 FIG.6A PHOTOINTERRUPTER OUTPUT (20)
 FIG.6B PHOTOINTERRUPTER OUTPUT (21)
 FIG.6C BURNOUT SENSOR OUTPUT
 FIG.6D INVERTING CIRCUIT OUTPUT
 FIG.6E MONOSTABLE MALTI-VIBRATOR OUTPUT
 FIG.6F STOP CIRCUIT OUTPUT
 FIG.6G COUNTER OUTPUT
 FIG.6H INTEGRATION CIRCUIT OUTPUT
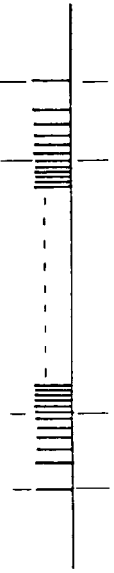 FIG.6I V/F CONVERTER OUTPUT

LIGHT-SOURCE SWITCHING AND DRIVING UNIT

BACKGROUND OF THE INVENTION

This application claims the priority of Japanese Patent Application No. 7-183558, filed on Jun. 27th, 1995 which is incorporated herein by reference.

1. Field of the Invention

The present invention relates to a light-source switching and driving unit, and more particularly to a drive unit which performs switching of light-source lamps in a light source device that is utilized in medical or industrial endoscopes, etc.

2. Description of the Related Art

In medical or industrial endoscopes, there is used a light source device for illuminating the interior of a body to be observed. In a case where an incandescence lamp is used in this kind of light source device as a light-source lamp, the light-source lamp is often burned out. For this reason, a plurality of lamps, including spare lamps, have hitherto been attached movably. When the lamp being currently used is burned out, a spare lamp is moved to the used position. According to this, satisfactory observation would become possible without interrupting the operation of the endoscope even if the light-source lamp were burned out.

However, the aforementioned conventional light-source device uses a DC motor as a driving means for switching light-source lamps and this DC motor has the following disadvantages. That is, it is difficult to accurately stop the light-source lamp at a target position, and furthermore, because the conventional device does not have a lamp holding function, it is almost impossible to hold a position where the light-source lamp is stopped. For this reason, an additional mechanical structure, or an assisting means, such as a stop device and a holding device using an electromagnetic clutch or a solenoid, is provided. However, in such a case, the device becomes structurally complicated and the size of the device is increased. Furthermore, sufficiently high reliability has not been obtained yet.

SUMMARY OF THE INVENTION

The present invention has been made in view of the problems described above. It is accordingly the object of the present invention to provide a light-source switching and driving unit which uses a stepping motor having both an accurate stop operation and a strong holding force and where noise and an impact to light-source lamps, which are caused by the use of the stepping motor, can be prevented with a simple structure.

To this end, there is provided a light-source switching and driving unit, which comprises a plurality of light-source lamps disposed for being switched and used, moving means for moving said plurality of light-source lamps to a predetermined position, a stepping motor for operating said moving means, and pulse generating means for generating a pulse which drives said stepping motor, the drive pulse being gradually increased when said stepping motor is started or being gradually decreased when said stepping motor is stopped.

It is preferable that the pulse generating means be constructed such that a drive pulse which gradually increases is generated when the stepping motor is started and also a drive pulse which gradually decreases is generated when the stepping motor is stopped.

The light-source switching and driving unit may further comprise a burnout sensor which detects that the light-source lamp being currently used is burned out. The light-source lamp being currently used may be switched to another light-source lamp, based on an output of the burnout sensor.

The pulse generating means may be constituted by an integration circuit which generates a voltage that gradually varies and a voltage/frequency converter which generates a drive pulse that gradually increases or decreases, based on an output voltage from the integration circuit.

Furthermore, the pulse generating means may be provided with a counter which counts a number of the drive pulses, and the drive pulse which gradually decreases may be generated by the counter at the time the counter has counted a number of drive pulses which indicates a position which is a predetermined quantity short of a position at which the stepping motor is stopped.

The present invention proposes that a stepping motor is used as a drive means for switching light-source lamps. With this stepping motor, it is easy to accurately stop the light-source lamp at a target position, and also a strong holding force is obtained. The present invention, therefore, has the advantage that the stopped position of the light-source lamp can be held satisfactorily.

On the other hand, the stepping motor has the disadvantage that noise will be generated from the motor itself and a rotation transferring means, because the stepping motor is stepped to move the lamp to a predetermined position. In addition, since it is characteristic of a stepping motor to be rapidly started and stopped, there is the problem that a strong impact will be applied to a light-source lamp which is an object of movement when the stepping motor is started up and stopped and that the life of the lamp is shortened. Furthermore, if a special rotation transferring means for reducing the aforementioned noise, or a special lamp mounting means for absorbing the aforementioned impact, is used as a countermeasure, then the structure will become complicated as in the case of the aforementioned DC motor.

Then, as described above, the pulse generating means is provided so that a drive pulse is formed which gradually increases when the motor is started up or gradually decreases when the motor is stopped. More specifically, an electrical signal which gradually increases or decreases is formed by the aforementioned integration circuit, and if this electrical signal is converted to a frequency signal by the voltage/frequency converter, then a drive pulse (number of pulses per unit time) which gradually increases can be generated, or a drive pulse (number of pulses per unit time) which gradually decreases can be generated. Therefore, when the stepping motor is driven by this drive pulse, the light-source lamp moves at a speed which is gradually accelerated when the motor is started up, and moves a speed which is gradually decelerated when the motor is stopped. Thus, a lamp moving operation which is not rapid is obtainable.

The above and other objects and advantages of the present invention will become apparent from the following detailed description when read in conjunction with the accompanying drawings.

BRIEF DESCRIPTION OF THE DRAWINGS

FIG. 4 is a timing diagram showing the operation of the light-source switching and driving unit of FIG. 1;

FIG. 6 is a timing diagram showing the operation of the light-source switching and driving unit of FIG. 5.

DETAILED DESCRIPTION OF THE PREFERRED EMBODIMENTS

First Embodiment

Figure 1:
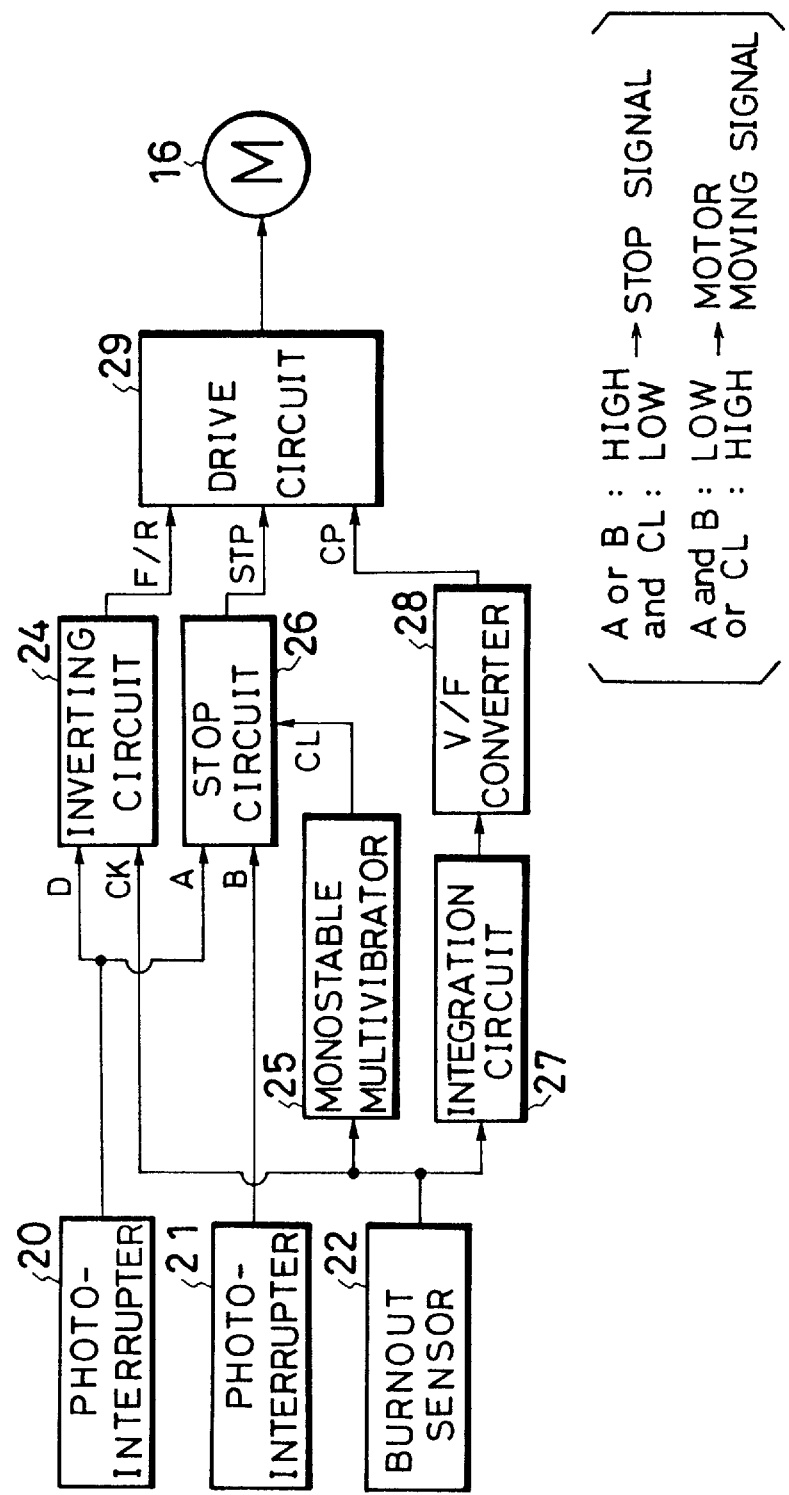
FIG. 1 is a block diagram showing a light-source switching and driving unit constructed in accordance with a first embodiment of the present invention.
Figure 2:
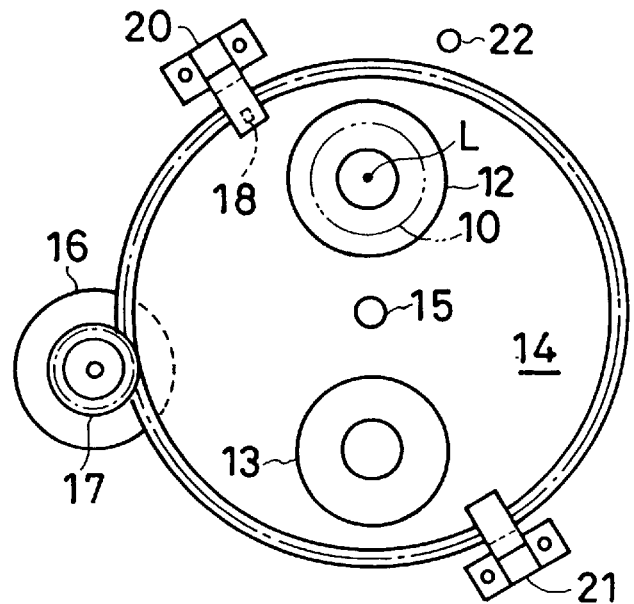
FIG. 2 is a bottom view showing the light-source switching and driving unit of FIG. 1.
Figure 3:
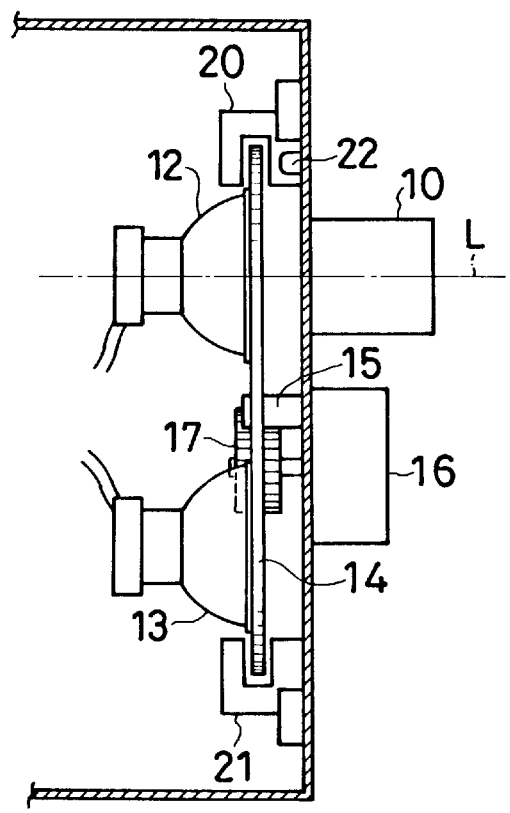
FIG. 3 is a side elevational view showing the light-source switching and driving unit of FIG. 1.

Referring now in greater detail to the drawings and initially to FIGS. 1 through 3, there is shown a preferred embodiment of a light source switching drive unit in accordance with the present invention. This unit is applied to endoscopes, etc. In FIGS. 2 and 3, a light guide connector 10 is a connector for a light guide disposed in an endoscope for guiding light to the distal end of the endoscope. The optical axis of a light source lamp (hereinafter referred to simply a lamp) 12 is aligned with the optical axis of the light guide in order to guide light. More specifically, this lamp 12, together with another spare light source lamp 13, is attached to a turn table 14 where the outer circumference is formed into a gear. By rotating this turn table 14 with a shaft 15 as a center, the two lamps 12 and 13 can be selectively moved into the position of the aforementioned optical axis L.

A stepping motor 16 is used as a drive means, and a gear 17 mounted on the shaft of the stepping motor 16 is disposed so that it can mesh with the outer circumferential gear portion of the turn table 14.

The turn table 14 is provided with a single sensing aperture 18, and a first photointerrupter 20 is disposed at a position where the sensing aperture 18 is detected when the optical axis of the lamp 12 is aligned with the optical axis L. Likewise, a second photointerrupter 21 is disposed at a position where the sensing aperture 18 is detected when the optical axis of the spare lamp 13 is aligned with the optical axis L. That is, each photointerrupter, as shown in FIG. 3, is positioned over both surfaces of the outer circumference of the turn table 14 so that it can detect the existence of the sensing aperture 18 by the state of the light transmitted through the sensing aperture 18.

A burnout sensor 22 for sensing the burnout state of the lamp 12 is provided in the upper front of the lamp 12. The burnout sensor 22 detects the light from the lamp 12 in use and discriminates the burnout state. The burnout senor 22 has been set so that a logic high signal is obtained only when the lamp 12 in its lighted state is burned out and also a logic low signal is obtained when the lamp 12 is in the lighted or non-lighted state.

In the embodiment shown in FIG. 1, the output of the first photointerrupter 20 is input to the D input of an inverting circuit 24 and also to the A input of a stop circuit 26. The output of the second photointerrupter 21 is input to the B input of the stop circuit 26. The output of the burnout sensor 22 is input to the CK input of the inverting circuit 24 and also to the CL input of the stop circuit 26 through a monostable multivibrator 25. The output of the burnout sensor 22 is further input to an integration circuit 27, which in turn is connected to a voltage/frequency (V/F) converter 28. The output of the inverting circuit 24, the output of the stop circuit 26, and the output of the V/F converter 28 are input to the F/R, STP, and CP inputs of a drive circuit 29, respectively.

That is, the inverting circuit 24 is constituted by a D flip-flop circuit, etc. When the D input of the inverting circuit 24 (the output of the photointerrupter 20) is triggered at a logic high level and the CK input (the output of the burnout sensor 22) at a logic high level, the inverting circuit 24 outputs a signal which causes the stepping motor 16 to rotate, for example, in a clockwise direction (in the state of FIG. 2). When, on the other hand, the D input is triggered at a logic low level and the CK input at a logic low level, the inverting circuit 24 outputs a signal which causes the stepping motor 16 to rotate in a counterclockwise direction.

The aforementioned stop circuit 26 is an arithmetic logic circuit. When either the aforementioned A input (the output of the first photointerrupter 20) or B input (the output of the second photointerrupter 21) is at a logic high level (when either photointerrupter is disposed in a position on the optical axis L) and also when the CL input (to which a signal, where the output state of the burnout sensor 22 was held at the monostable multivibrator 25 for a predetermined time, is input) is at a logic low level (lamp lighted state), the stop circuit 26 outputs a stop signal. When, on the other hand, the levels on the A input and the B input are both low (during movement) or when the level on the CL input is high (lamp burned-out state), the stop circuit 26 outputs a lamp moving signal.

The aforementioned integration circuit 27, when the lamp 12 or 13 in the lighted state is burned out and the burnout sensor 22 rises from a logic low level to a logic high level, outputs a voltage which increments, that is, rises gradually according to a time constant that was set. Then, the V/F converter 28 generates a drive pulse having a frequency proportional to the level of the output voltage of the integration circuit 27.

That is, when the output voltage of the integration circuit 27 is low, the V/F converter 28 outputs a pulse having a frequency of zero or a pulse with a frequency such that the aforementioned stepping motor 16 will be started at a speed in a region where an impact to be given to the lamps 12 and 13 can be neglected. Also, the aforementioned drive pulse increases gradually according to an increase in the output voltage level of the integration circuit 27, and after this voltage level attains a predetermined high voltage, the drive pulse is set to a frequency where the stepping motor 16 is in an area of a slewing torque and rotates under optimum conditions that the noise generated by movable mechanisms becomes minimum.

Finally, the aforementioned drive circuit 29 supplies a drive output to the stepping motor 16, based on output control signals from the inverting circuit 24, the stop circuit 26, and the V/F converter 28.

The first embodiment of the present invention is constituted as described above and the operation will hereinafter be described in reference to an operational waveform diagram of FIG. 4. When the center axis of the lamp 12 is aligned with the optical axis L and is lighted and used, as shown in FIGS. 2 and 3, the sensing aperture 18 is detected and the output of the first photointerrupter 20 goes to a high level, and conversely, the output of the second photointerrupter 21 goes to a low level. Also, the lighted state of the lamp 12 is detected and the output of the burnout sensor 22 goes to a low level. In this state, the stop circuit 26 outputs a stop signal to stop the stepping motor 16, and the state shown in FIG. 1 is maintained.

If the aforementioned lamp 12 is burned out during use such as this, then the output of the burnout sensor 22 will go from a low level to a high level, as shown in FIG. 4(C). As a result, because the CK input of the inverting circuit 24 is triggered at a high level, an output signal [FIG. 4(D)], which causes the stepping motor 16 to rotate, for example, in a clockwise direction, is supplied from the inverting circuit 24 to the F/R input terminal of the drive circuit 29. The output of the burnout sensor 22 is also input to the monostable multivibrator 25 and the integration circuit 27. If the output of the monostable multivibrator 25 is held at a high level for a predetermined time, as shown in FIG. 4(E), and is input to the CL input of the stop circuit 26, then an lamp moving signal [FIG. 4(F)] instead of the stop signal will be supplied from the stop circuit 26 to the STP input of the drive circuit 29.

In addition, a voltage, which gradually rises as shown in FIG. 4(G), is input from the integration circuit 27 to the V/F converter 28. In this V/F converter 28, a drive pulse which increases gradually in proportion to the aforementioned voltage is formed as shown in FIG. 4(H), and this drive pulse is supplied to the CP input of the drive circuit 29. As a consequence, the stepping motor 16 rotates in a clockwise direction and causes the turn table 14 to rotate by the gear 17 (in FIG. 2, in a clockwise direction). When this occurs, the turn table 14 starts at a speed which gives no impact to the lamps 12 and 13 and is slowly accelerated. If the speed of the turn table 14 gets into an area of the slewing torque of the stepping motor 16, then the speed of the turn table 14 will become constant at the time it reaches optimum conditions where the noise generated by the movable mechanisms becomes minimum.

Since the sensing aperture 18 shown in FIG. 2 is moved out of the detecting area of the photointerrupter 20 during the aforementioned operation, the output of the photointerrupter 20 changes to a low level, as shown in FIG. 4(A). Therefore, the A and B inputs of the stop circuit 26 both go to a low level, and even if the output of the monostable multivibrator 25 returned to a low level, the stop circuit 26 would maintain the output of the lamp moving signal. That is, the monostable multivibrator 25 serves to compensate the delay of the detection of the photointerrupter 20, and the time constant is set so that a high level is output only during the time until the output of the burnout sensor 22 goes to a high level and then the turn table 14 is started and the output of the photointerrupter 20 goes to a low level.

Thereafter, if the center axis of the lamp 13 is moved to the optical axis L by rotation of the turn table 14, the sensing aperture 18 will be detected by the second photointerrupter 21 and the output of the second photointerrupter 21 will change from a low level to a high level. Therefore, a stop signal is output from the stop circuit 26 (because the level on the CL input of the stop circuit is low), and since the input pulse of the drive circuit is cut off by the stop signal, the stepping motor stops and this stopped position is held, thereby disposing the lamp 13 on the side where the lamp is used.

Conversely, in a case where the lamp 13 is burned out during use, the output of the burnout sensor 22 (the CL input of the stop circuit 26) goes to a high level and the stop circuit 26 is caused to output a lamp moving signal. At the same time, the CK input of the inverting circuit 24 is triggered. On the other hand, because the first photointerrupter 20 does not detect the sensing aperture 18, the D input of the inverting circuit 24 goes to a low level. By inverting the output of the inverting circuit 24, the stepping motor 16 is rotated in the opposite direction, that is, in a counterclockwise direction. Therefore, in this case, the turn table 14 rotates in a counterclockwise direction (FIG. 2) and the center axis of the lamp 12 is moved to the position of the optical axis L. In this way, the lamp 12 is returned to the state shown in FIG. 2.

Second Embodiment

Figure 5:
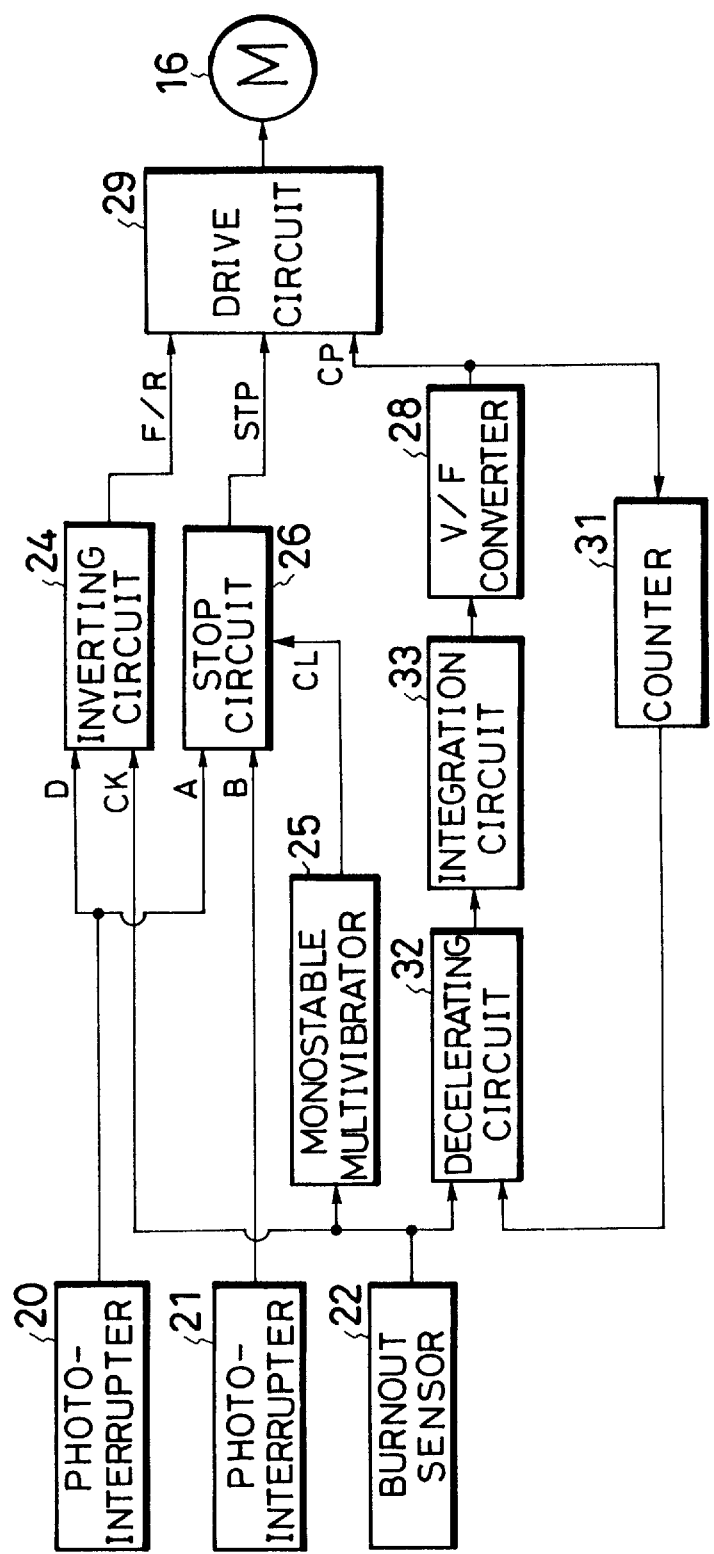
FIG. 5 is a block diagram showing a light-source switching and driving unit constructed in accordance with a second embodiment of the present invention.

FIG. 5 shows a block diagram of a second embodiment of the present invention. This embodiment uses a drive pulse which gradually reduces when the motor is stopped. The second embodiment, as shown in FIG. 5, adds a counter 31 and a decelerating circuit 32 to the constitution of FIG. 1. The counter 31 is connected so that the output of the V/F converter 28 is input, and counts the number of drive pulses which output from the V/F converter 28. More specifically, the counter 31 is constructed such that it outputs a low level signal to the decelerating circuit 32 when it counts out a set pulse number before a quantity of movement of the aforementioned lamp 12 or 13 attains a stop target position.

The decelerating circuit 32 outputs the same phase and voltage as the output of the burnout sensor 22 when the level on the output of the counter 31 is low and also outputs a low level signal independently of the output of the burnout sensor 22 when the level on the output of the counter 31 is low. When a signal which goes from a high level to a low level is input to the integration circuit 33 connected after the decelerating circuit 32, a voltage which gradually reduces is output to the V/F converter 28.

FIG. 6 shows an operation waveform of the second embodiment. The second embodiment is identical with the operation of the first embodiment as to the motor starting operation. As shown in FIG. 6(I), the motor is slowly started by a drive pulse which gradually increases. When the driving of the motor is stopped, a voltage which decrements as shown in FIG. 6(H) is output from the integration circuit 33, and as shown in FIG. 6(I), a drive pulse which gradually reduces is supplied from the V/F converter 28 to the drive circuit 17. Therefore, as shown in FIG. 6(J), the rotational speed of the stepping motor 16 starts reducing before it is stopped, and when the rotational speed becomes a speed at which an impact to be given to the lamps 12 and 13 can be neglected, the stepping motor 16 is stopped.

In this way, in the second embodiment, an impact to be given to the lamps and noise are considerably alleviated because a slow operation is executed not only when the motor is started but also when the motor is stopped. Note that, by making use of the gradually decreasing drive pulse of the second embodiment, a slow operation may be executed only when the motor is stopped.

While it has been described in the aforementioned first and second embodiments that gradually increasing or decreasing voltages have been formed by using the integration circuit 27 or 33, these gradually increasing and decreasing voltages can be formed and output by other circuits.

According to the present invention, as described above, noise can be reduced without providing a special rotation transferring means, or a lamp mounting means, which becomes structurally complicated, and at the same time, an impact with respect to the light-source lamp can be prevented and the life of the lamp can be lengthened. Furthermore, by adopting a stepping motor, there is the advantage that an accurate stopping operation and a strong holding force are obtained.

Moreover, if the aforementioned pulse generating means is constructed such that a drive pulse which gradually increases is generated when the stepping motor is started and also a drive pulse which gradually decreases is generated when the stepping motor is stopped, then further advantageous effect will be obtained.

What is claimed is:
1. A light-source switching and driving unit comprising:
   a plurality of light-source lamps disposed for being switched and used;

moving means for moving said plurality of light-source lamps to a predetermined position;

a stepping-motor for operating said moving means; and pulse generating means for generating a pulse which drives said stepping motor, the drive pulse being gradually increased when said stepping motor is started or being gradually decreased when said stepping motor is stopped.

2. The light-source switching and driving unit as set forth in claim 1, wherein said pulse generating means is constructed such that a drive pulse which gradually increases is generated when said stepping motor is started and also a drive pulse which gradually decreases is generated when said stepping motor is stopped.

3. The light-source switching and driving unit as set forth in claim 1, which further comprises a burnout sensor which detects that the light-source lamp being currently used is burned out and wherein said light-source lamp being currently used is switched to another light-source lamp, based on an output of said burnout sensor.

4. The light-source switching and driving unit as set forth in claim 1, wherein said pulse generating means includes an integration circuit which generates a voltage that gradually varies and also includes a voltage/frequency converter which generates a drive pulse that gradually increases or decreases, based on an output voltage from said integration circuit.

5. The light-source switching and driving unit as set forth in claim 1, wherein said pulse generating means is provided with a counter which counts a number of the drive pulses and wherein said drive pulse which gradually decreases is generated by said counter at the time said counter has counted a number of drive pulses which indicates a position which is a predetermined quantity short of a position at which the stepping motor is stopped.

6. An endoscope light-source switching and driving unit comprising:

a plurality of light-source lamps disposed on the endoscope for being switched and used;

a moving means for moving said plurality of light-source lamps to a predetermined position;

a stepping motor for operating said moving means; and pulse generating means for generating a pulse which drives said stepping motor, the drive pulse being gradually increased when said stepping motor is started or being gradually decreased when said stepping motor is stopped.

7. The endoscope light-source switching and driving unit as set forth in claim 6, wherein said pulse generating means is constructed such that a drive pulse which gradually increases is generated when said stepping motor is started and also a drive pulse which gradually decreases is generated when said stepping motor is stopped.

8. The endoscope light-source switching and driving unit as set forth in claim 6, which further comprises a burnout sensor which detects that the light-source lamp being currently used is burned out and wherein said light-source lamp being currently used is switched to another light-source lamp, based on an output of said burnout sensor.

9. The endoscope light source switching and driving unit as set forth in claim 6, wherein said pulse generating means includes an integration circuit which generates a voltage that gradually varies and also includes a voltage/frequency converter which generates a drive pulse that gradually increases or decreases, based on an output voltage from said integration circuit.

10. The endoscope light-source switching and driving unit as set forth in claim 6, wherein said pulse generating means is provided with a counter which counts a number of the drive pulses and wherein said drive pulse which gradually decreases is generated by said counter at the time said counter has counted a number of drive pulses which indicates a position which is a predetermined quantity short of a position at which the stepping motor is stopped.

* * * * *